United States Patent [19]

Ogawa et al.

[11] Patent Number: 5,942,487
[45] Date of Patent: Aug. 24, 1999

[54] COMPOSITION FOR TREATING CORNEA

[75] Inventors: Takahiro Ogawa, Nishinomiya; Hideki Tokushige, Kobe; Noriko Watanabe, Suita, all of Japan

[73] Assignee: Senju Pharmaceutical Co., Ltd., Osaka, Japan

[21] Appl. No.: 08/976,088

[22] Filed: Nov. 21, 1997

[30] Foreign Application Priority Data

Nov. 29, 1996 [JP] Japan .................................. 8-334667

[51] Int. Cl.$^6$ .................................................. A61K 31/00
[52] U.S. Cl. ............................................. 514/2; 514/912
[58] Field of Search ........................................ 514/2, 912

[56] References Cited

FOREIGN PATENT DOCUMENTS

WO91/05795  5/1991  WIPO .
WO92/14480  9/1992  WIPO .

*Primary Examiner*—Zohreh Fay
*Attorney, Agent, or Firm*—Wenderoth, Lind & Ponack, L.L.P.

[57] ABSTRACT

A pharmaceutical composition comprising a stem cell factor (SCF) is administered systemically or locally, preferably administered locally to the eye surface to promote the healing of corneal disorder or injured part in comparison with untreated control.

2 Claims, 1 Drawing Sheet

Fig. 1. The effect of rmSCF on the healing of corneal epithelial defect. (n=9, mean +/- S.E., * : p<0.05, ** : p<0.01)
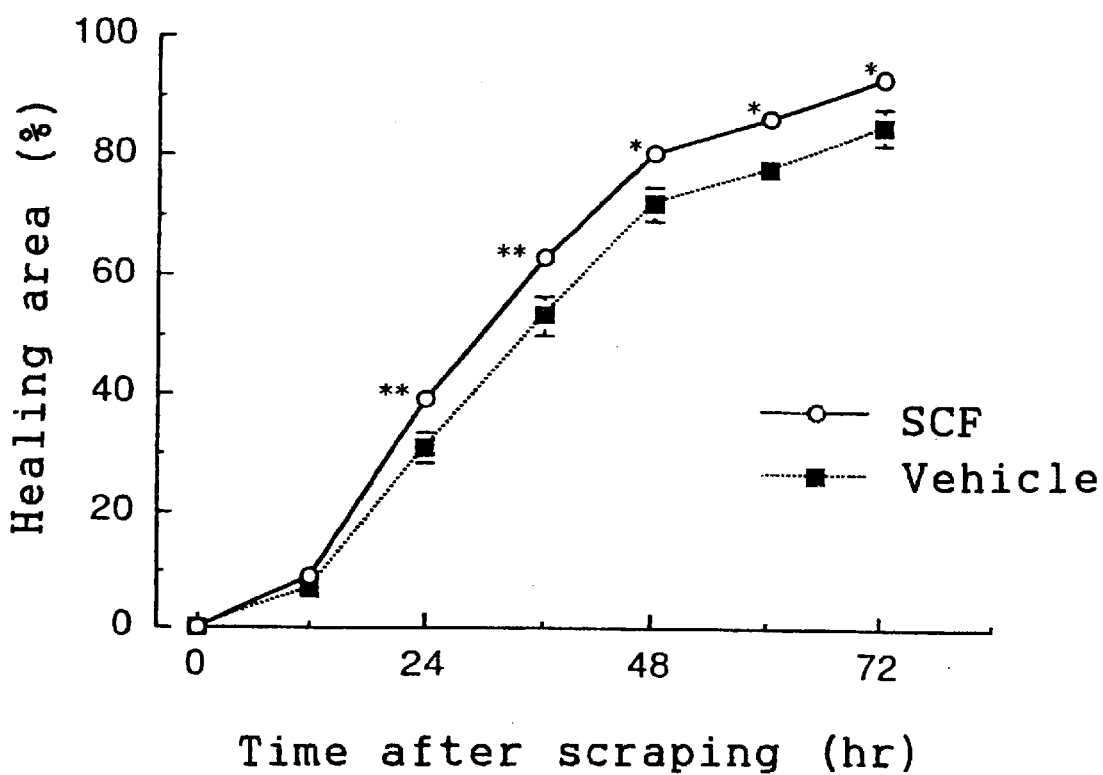

COMPOSITION FOR TREATING CORNEA

FIELD OF THE INVENTION

The present invention relates to a composition for treating cornea, and more particularly, relates to a composition which promotes the corneal epithelial healing.

BACKGROUND OF THE INVENTION

Cornea is a transparent avascular connective tissue composed of 5 layers consisting of epithelium, Bowman's membrane, stroma, descemet's membrane and endothelium.

Corneal epithelium, the most outer layer of cornea is a tissue having a thickness of about 50 μm composed of 5 to 6 layers of cells, and occupies about one-tenth of the thickness of cornea. This corneal epithelium can be divided into three groups, a superficial cell, wing cell and basal cell from anatomical aspect. The superficial cell is a flat polygonal cell composed of 2 to 3 layers situated on the most outer surface, and has a length of about 40 μm and a thickness of about 4 μm. On the surface of the superficial cell, there is seen small projections, which enhance adhesion of a lacrimal layer, particularly a mucin layer thereof and enlarge the surface area for easy diffusion and active transport of a material from the lacrimal fluid.

In cytoplasm of a superficial cell, there are seen a few mitochondria and a lot of glycogen granules. The superficial cells firmly adhere to each other and form an important barrier to prevent the invasion of foreign materials including bacteria.

The wing cell is under the superficial cell, and exists in intermediate process wherein the cell pushed out from a basal cell layer is gradually flattened to become a superficial cell. The cells are adhered to each other with desmosome and mutual insertion between the cells is observed.

The basal cells form a layer, the lowest layer of corneal epithelium, and are polyhedral cells having a height of about 18 μm and a width of about 10 μm. A cell mitosis is active, a daughter cell resulting from mitosis becomes a wing cell, and further turns into a superficial cell is finally exfoliated from the corneal surface. It is said that the period of this cycle is about 1 to 2 weeks. In a cell membrane in the base part of the basal cell, there is an adhesion means called hemidesmosome and it adheres to a basement membrane below. Hemidesmosome, basement membrane and anchoring fibril below play an important role in adhesion of corneal epithelium. The basement membrane has a thickness of about 50 to 60 μm formed by the basal cells, and composed of Type IV collagen, laminin, heparan sulfate and the like.

Corneal epithelium is sometimes lost because of various reasons. Corneal epithelial defect can be clinically classified into simple epithelial defect, recurrent epithelial defect and persistent epithelial defect.

The simple epithelial defect occurs when an epithelial cell is deleted or decomposed for example by dry eye, corneal infective disease, stem cell depletion syndrome, injury and the like.

Diseases caused by dry eye include Riley-day syndrome, Shy-Drager syndrome, Sjögren syndrome, sarcoidosis, amyloidosis, sequela of radiotherapy, lagophthalmia, avitaminosis A, Stevens-Johnson syndrome, ocular pemphigoid, marginal blepharitis, meibomitis, sequela of intraocular surgery, contact-lens affection, diabetic corneal epitheliopathy, dry eye due to VDT operation and the like.

Disorder caused by corneal infective disease includes for example viral epitheliopathy and the like.

The stem cell depletion syndrome includes Stevens-Johnson syndrome, ocular pemphigoid, thermal or chemical burn, drug toxicity of idoxuridine (IDU) and therapeutical agents for glaucoma and the like.

The recurrent epithelial defect is caused, for example, by reduction in adhesion of a epithelial cell to stroma due to recurrent corneal epithelial erosion (including injury), map-dot-fingerprint dystrophy, grill-like corneal dystrophy, Reis-Buecklers corneal dystrophy, diabetic corneal epitheliopathy and the like.

The persistent epithelial defect is caused by disorder in migration of a epithelial cell due to, for example, chemical burn, neurotrophic keratitis, corneal infective disease, toxicity of anti-viral agent and anti-microbial agent.

It has been generally believed that when such corneal disorders, particularly wound and defect occur on corneal epithelium, healing and regeneration can be achieved only by proliferation of a basal cell in corneal epithelium, however, recent influential theory is that a stem cell existing in corneal limbus prolifirates and migrates gradually towards central part of cornea and then, the cell is pushed out on the surface of cornea for regeneration of corneal epithelium [Schermer A. et al., J. Cell. Biol. 103: 49 to 62 (1986)]. Limbal epithelium exists spreading for a length of about 1 mm in corneal limbal portion which is a transition part from conjunctival epithelium to corneal epithelium, and in human, forms a specific wrinkled structure called POV (Palisades of Vogt). This limbal epithelium occupies about one-forth in the area of cornea, and differs from conjunctival epithelium in that there is no goblet cell and differs from corneal epithelium also in that a subepithelial tissue contains a blood vessel and Langerhan's cell and melanocyte exist. Further, the stem cell of corneal epithelium is believed to exist therein. In fact, when such limbal epithelium regenerates on cornea, it forms epithelium having the same function as normal corneal epithelium.

According to a rabbit experiment, after corneal epithelial defect is caused, limbal epithelium quickly repeats cell migration and proliferation, and primary healing of epithelium is completed in about 4 to 5 days. After that, epithelial proliferation continues for several days, and the thickness increases gradually and the same construction as normal corneal epithelium is formed in about 2 weeks. Though, it is a feature of regenerated conjunctival epithelium that an goblet cell is recognized in regenerated epithelium, such an goblet cell is not produced in the regeneration process. Thus, regeneration in a limbal epithelium extremely resembles regeneration in corneal epithelium in surrounding parts. However, it has been revealed that regenerated limbal epithelium two weeks after healing is not the same as the regenerated corneal epithelium. For example, it is also said that there is a little difference between their intraepithelial protein patterns while an electron-microscopic observation of the regenerated limbal epithelium somewhat resembles that of conjunctiva. Further, it is reported that migration of the epithelium regenerated from limbal epithelium are suppressed by steroid, however, they are not suppressed in the case of regenerated corneal epithelium.

In this way, the regenerated limbal epithelium in early phase after wound healing seems slightly different from corneal epithelium, however, it is considered that the same cell formation function as corneal epithelium is recovered in the long term.

In either case, when wound or defect occurs in cornea, there are fears that crisis of corneal infection increases, corneal ulcer, corneal stromal opacity and the like are caused, and a serious disorder in visual function is caused. Therefore, when wound or defect occurs in corneal epithelium, it is important to repair them as fast as possible.

However, at the present time, there are only nosotropic means like equipping with a compression eye bandage or soft contact lens, application of an eye ointment and the like, against wound and defect of corneal epithelium, and consequently, it is strongly desired to positively establish the treating methods.

SUMMARY OF THE INVENTION

The present inventors have intensively studied seeking means by which, when a part or all of corneal epithelium is injured, the healing and regeneration thereof should be promoted, and a depletive stem cell should be activated and corneal epithelium should recover normal condition as fast as possible.

As a result, the present inventors have confirmed experimentally that a stem cell factor (hereinafter, sometimes abbreviated as SCF) which is known as one possessing an action promoting proliferation and differentiation of a hematopoietic stem cell has an action promoting corneal epithelial healing, and have further investigated to complete the present invention.

Namely, the present invention provides
(1) A composition for treating cornea which comprises SCF and a pharmaceutically acceptable carrier,
(2) The composition according to said (1), wherein the composition for treating cornea is a composition which promotes the corneal epithelial healing,
(3) The composition according to said (1), wherein SCF is a product of a recombinant prokaryote cell or eukaryote cell,
(4) The composition according to said (1), wherein SCF is human SCF,
(5) The composition according to said (1), which contains at least one protein selected from the group consisting of EGF, FGF, GM-CSF, IGF-I, IGF-II, insulin, interferon, interleukin, KGF, M-CSF, PD-ECGF, PDGF, G-CSF, TGF-α and TGF-β,
(6) The composition according to said(1), wherein the composition for treating cornea is an ophthalmic drop,
(7) The composition according to said (1), wherein the composition for treating cornea is an ophthalmic ointment,
(8) A method of promoting corneal healing which comprises administering an effective amount of a composition comprising SCF and a pharmaceutically acceptable carrier to a subject suffering from corneal disorder, and
(9) The method according to said (8), wherein the corneal disorder is corneal epithelial defect.

DETAILED DESCRIPTION OF THE INVENTION

The term "stem cell factor" or "SCF" which is used in the present invention refers to natural SCF (for example, natural human SCF), and a non-natural polypeptide which is glycosylated or has an amino acid sequence which can overlap with that of natural SCF so that it has the biological hematopoietic activity of natural SCF. This SCF is described in detail in Patent Kohyo Publication 502628/1992 (WO 91/05795), which is incorporated herein for reference.

Namely, this SCF is a factor having an ability to stimulate proliferation of a primitive precursor cell including early hematopoietic precursor cell, and it is known that when a mammal is treated with this factor, an increase is caused in the number of hematopoietic cells in bone marrow like and lymphocyte like line.

In the present invention, a composition for treating cornea containing SCF is administered locally or systemically to a patient suffering from the above-described disorders in cornea. This pharmaceutical composition includes pharmaceutical compositions containing a suitable diluent, preservative, solubilizer, emulsifier, adjuvant and/or carrier, together with therapeutically effective amount of SCF. The term "therapeutically effective amount" as used in the present specification refers to an amount which provides therapeutic effect on the stipulated conditions and dosage regimen. Such a composition is in a liquid, freeze-dried or dried form, which includes various buffering agents (for example, tris-hydrochloric acid, acetate, phosphate), diluents having various pH and ionicity, additives such as albumin or gelatin to prevent adhesion to the surface, surfactants (for example, Tween 20, Tween 80, Pluronic F68, bile salt), solubilizers (for example, glycerin, polyethylene glycol), antioxidants (for example, ascorbic acid, sodium meta bisulfite), preservatives (for example, thimerosal, benzyl alcohol, parabenes), fillers or isotonic agent (for example, lactose, mannitol), intake of said materials into covalent bondage formation of a polymer such as polyethylene glycol to protein, complex formation with a metal ion, a granular preparation of a polymer compound such as polylactic acid, polyglycolic acid, hydrogel and the like or onto the surface thereof, a nucleus of liposome, microemulsion, micelle minelayer or multilayer follicle, erythrocyte ghost or spheroplast.

The composition exerts an influence on physical conditions, solubility, stability, in vivo releasing speed, and in vivo clearance of SCF. Selection of dosage form depends on physical and chemical properties of the protein having SCF activity. For example, when the composition comprises SCF material obtained from its membrane bonding embodiment, it preferably contains a surfactant. As a controlled or sustained release composition, there are listed compositions contained in lipophilic depot preparations (for example, fatty acid, wax, oil). Further, the composition for the present invention includes a granular composition coated with a polymer (for example, poloxamer or poloxamine) and SCF which bonds to a tissue-specific receptor, antibody against ligand or antigen, or a ligand of the tissue-specific receptor.

The examples of specific formulations of the present composition include systemic administering agent for example parenteral, transpulmonary, transnasal and oral, and local administering agents for example eye drops and eye ointments.

SCF used in the present invention can further promote the corneal epithelial healing in combination with at least one member selected from the group consisting of EGF, FGF, GM-CSF, IGF-I, IGF-II, insulin, interferon, interleukin, KGF, M-CSF, PD-ECGF, PDGF, TGF-α and TGF-β.

To promote the healing of disordered corneal epithelium, it is often effective to administer a composition for treating cornea in the form of a local administering agent, namely an eye drop or eye ointment to the surface of eye.

The eye drop is provided in any formulation generally used, for example, in the form of an aqueous eye drop such as aqueous eye drop solution, aqueous eye drop suspension, viscous eye drop solution, solubilized eye drop solution and the like, or in the form of a non-aqueous eye drop such as a non-aqueous eye drop solution, non-aqueous eye drop suspension and the like.

When the composition for treating cornea of the present invention is prepared as an aqueous eye drop, it preferably contains an additive which is usually used in an aqueous eye drop. The examples of such an additive include preservatives, isotonic agents, buffering agents, stabilizer, pH regulators or the like.

The examples of the preservative used include parabenes (methyl para-oxy benzoate, propyl para-oxy benzoate and the like), inverted soaps (for example, benzalkonium chloride, benzetonium chloride, chlorohexydine gluconate, cetylpiridinium chloride and the like), alcohol derivatives (for example, chlorobutanol, phenetyl alcohol, benzyl alcohol and the like), organic acids and salts thereof (for example, sodium dehydroacetate, sorbic acid and salts thereof, and the like), phenols (for example, para-chloromethoxy phenol, para-chlorometa-cresol and the like), organic mercury agents (for example, thimerosal, phenylmercuric nitrate, nitromersol and the like.

The examples of the isotonic agent include sodium chloride, sorbitol, mannitol, glycerin and the like, the examples of the buffering agent include phosphate, borate, citrate, acetate, salt of amino acid and the like, the examples of the stabilizer (chelating agent) include sodium edetate, sodium citrate, condensated sodium phosphate, sulfite and the like, and the examples of the pH regulator used include hydrochloric acid, acetic acid, sodium hydroxide, phosphoric acid and the like.

Further, a water-soluble high-molecular substance, surfactant and the like are suitably blended for the preparation. The examples of the water-soluble high-molecular substance include cellulose derivatives, vinyl-based polymer compounds, polyvalent alcohol compounds and the like, the examples of the cellulose derivative used include alkyl celluloses such as methyl cellulose, carboxymethyl cellulose and the like, hydroxyalkyl celluloses such as hydroxypropylmethyl cellulose, hydroxyethyl cellulose and the like, and the examples of the vinyl-based polymer compound used include polyvinyl pyrrolidone, polyvinyl alcohol, carboxylvinyl polymer, ethylene maleic anhydride polymer and the like, and the examples of the polyvalent alcohol compound include polyethylene glycol (macrogol), propyleneglycol and the like. The examples of the surfactant include polysorbates, nonionic surfactants such as polyoxyethylene hardened castor oil and the like, cationic surfactants such as quaternary ammonium salt and the like, anionic surfactants such as alkyl sulfate and the like, amphoteric surfactants such as lecithin and the like.

When the composition for treating cornea of the present invention is prepared as an aqueous suspension for eye drop solution, there is used a suspending agent which is usually used in an aqueous eye drop suspension. The examples of the suspending agent include methyl cellulose, sodium carboxymethyl cellulose, carboxyvinyl polymer, hydroxypropylmethyl cellulose, polyvinyl alcohol, polyvinyl pyrrolidone, polyethylene glycol (macrogol), sodium chondroitin sulfate, polysorbate 80 and the like.

When the composition of the present invention is an eye drop, it is advantageous to regulate the pH value thereof within the usual range used for eye drop preparation, and it is usually regulated from pH 3 to 8, preferably from pH 4 to 7. For this regulation, for example, hydrochloric acid, acetic acid, sodium hydroxide and the like are used.

It is advantageous that the osmotic pressure of the composition of the present invention is adjusted to the range usually employed for eye drop preparation, and it is usually from 230 to 450 mosm, and preferably from 260 to 320 mOsm. For this adjustment, for example, sodium chloride, boric acid, glycerin, mannitol and the like are used.

When the composition is used in a form of an eye ointment, it includes any formulations usually used. For example, it can be easily produced by optionally heating an eye ointment base and mixing it with SCF. SCF may be optionally dissolved or suspended in a suitable solvent, for example, sterilized pure water, distilled water for injection, vegetable oil such as castor oil and the like, before mixing with the eye ointment base.

The examples of the eye ointment base agent include purified lanolin, Vaseline, plastibase, liquid paraffin and the like. The above-mentioned preservative, stabilizer and the like can be optionally blended provided the object of the present invention is not hurt.

The diseases which are treated effectively by administration of the composition for treating cornea of the present invention include the above-described corneal disorders, specifically, simple epithelial defect including dry eye syndrome such as Riley-day syndrome, Shy-Drager syndrome, Sjögren syndrome, sarcoidosis, amyloidosis, sequela of radiotherapy, lagophthalmia, avitaminosis A, Stevens-Johnson syndrome, ocular pemphigoid, marginal blepharitis, meibomitis, sequela of intraocular surgery, contact lens affection, diabetic corneal epitheliopathy, dry eye due to VDT operation and the like; corneal infective disease such as viral epitheliopathy and the like; stem cell depletion syndrome such as Stevens-Johnson syndrome, ocular pemphigoid, thermal or chemical burn, drug toxicity of idoxuridine (IDU) and therapeutical agents for glaucoma, and the like; recurrent epithelial defect including recurrent corneal epithelial erosion (including injury), map-dot-fingerprint dystrophy, grill-like corneal dystrophy, Reis-Buecklers corneal dystrophy, diabetic corneal epitheliopathy and the like; and persistent epithelial defect caused by chemical burn, neurotrophic keratitis, corneal infective disease, toxicity of anti-viral and anti-microbial agents. Among them, the composition is particularly suitable for treatment of diseases due to stem cell depletion.

When the pharmaceutical composition of the present invention is administered to a patient suffering from the disease to be treated in an therapeutically effective amount, the corneal epithelial disorder is healed more quickly as compared with a patient to which the pharmaceutical composition is not administered.

In the present invention "therapeutically effective amount" is determined by an attendant physician or veterinarian on a patient. This amount can be easily determined by those skilled in the art, and if the composition is administered according to the present invention, wound is quickly cured. The examples of factors influencing the therapeutically effective amount include specific activity of the composition used, causes and kinds of the disorder, size of epithelial defect, depth of wound, presence or absence of infection, time after injuring, age, physical conditions, other disease conditions and nutriture of the term patient. Further, other pharmaceuticals administered to the term patient may exert an influence on the therapeutically effective amount of the drug. The "pharmaceutically acceptable" as used herein indicates that components other than the effective components contained in the formulation are suitable for administration to a patient which is cured according to the present invention.

When the composition for treating cornea of the present invention is an eye drop, the concentration of SCF is usually from 0.0001 to 10 w/v %, preferably from 0.001 to 1 w/v %, and when the composition is an eye ointment, the concentration of SCF is usually from 0.0001 to 10 w/w %, preferably from 0.001 to 1 w/w %.

When SCF is used in drug formulation suitable for administration to a patient, pharmaceutically acceptable aids and diluents can be contained. In the case of systemic administration, therapeutically effective amount of the drug is administered parenterally, for example subcutaneously, intravenously, intramuscularly, and intraperitoneally. For treatment of wound by parenteral administration, the composition is administered in a single dose, multiple doses or continuously depending on various factors, for example, the type, severity and part of wound.

According to the preferable embodiment of the present invention, SCF can be topically administered to promote corneal epithelial healing of a patient. This topical administration may be conducted once or repeatedly at multiple intervals. The preferable administration method depends on the type and degree of wound to be cured. Even if the composition is topically administered in a single dose, the wound is cured in remarkably short time as compared with the same wound which is not treated. When wound is infected or granulates chronically, the wound is cured in shorter time by repeated administration of the drug daily as compared with the same wound which is not treated.

To produce SCF in sufficient amount to be used for a commercial drug, these proteins are produced as products in which a recombinant prokaryote host cell or eukaryote host cell is manifested. Since a biologically active type of SCF can be recovered in large amount when prokaryote host cell, for example, E. coli is transformed with a suitable expression vector which encodes these polypeptides, and proliferation is conducted under conditions in which an extraneous gene is expressed, it is preferable to use SCF produced by this method.

EXAMPLE

The following working examples and test examples further illustrate the present invention in detail but are not to be construed to limit the scope thereof.

Example 1 Aqueous eye drop (1)

Preparation of an aqueous eye drop containing recombinant human SCF (rhSCF) as an effective component Formulation

| | |
|---|---|
| rhSCF | 1 mg |
| sodium acetate | 50 mg |
| benzalkonium chloride | 5 mg |
| sodium chloride | 650 mg |
| human serum albumin | 100 mg |
| sodium hydroxide | q.s. |
| diluted hydrochloric acid | q.s. |

Sterilized pure water was added to make a total amount 100 ml (pH 6.0)

Preparation Method

Sterilized pure water (80 ml) was heated, benzalkonium chloride was added and dissolved, then, sodium acetate, sodium chloride, sodium hydroxide and diluted hydrochloric acid were added in succession and dissolved. To the solution were further added rhSCF and human serum albumin and they were dissolved completely. The resulted solution was cooled down to room temperature, then sterilized pure water was added to make a total amount of 100 ml, and the mixture was filtered to be sterilized with a 0.22 μm membrane filter, and a container was filled with the filtrate to prepare an aqueous eye drop.

Example 2 Aqueous eye drop (2)

Preparation of an aqueous eye drop containing rhSCF as an effective component Formulation

| | |
|---|---|
| rhSCF | 1 mg |
| boric acid | 1.6 g |
| sodium tetraborate | 0.7 g |
| methyl para-oxybenzoate | 0.026 g |
| propyl para-oxybenzoate | 0.014 g |
| human serum albumin | 100 mg |

Sterilized pure water was added to make a total amount 100 ml. (pH 7.5)

Preparation Method

Sterilized pure water (80 ml) was heated, methyl para-oxybenzoate and propyl para-oxybenzoate were added and dissolved, then, the mixture was cooled. To this solution were added boric acid and sodium tetraborate in succession to be dissolved, further added rhSCF and human serum albumin to be dissolved completely. Sterilized pure water was added to this solution to make a total amount of 100 ml, and the mixture was filtered to be sterilized with a 0.22 μm membrane filter, and a container was filled with the filtrate to prepare an aqueous eye drop.

Example 3 Aqueous eye drop of optionally dissolved type(3)

Preparation of an aqueous eye drop to be dissolved at the time when used containing rhSCF as an effective component Formulation

| | |
|---|---|
| Freeze dried preparation | |
| rhSCF | 10 mg |
| human serum albumin | 1 g |
| Sterilized pure water was added to make a total amount | 100 ml. |
| Dissolving solution | |
| sodium acetate | 50 mg |
| benzalkonium chloride | 5 mg |
| sodium chloride | 650 mg |
| sodium hydroxide | q.s. |
| diluted hydrochloric acid | q.s. |

Sterilized pure water was added to make a total amount 100 ml. (pH 6.0)

Preparation Method

To 100 ml of sterilized pure water were added rhSCF and human serum albumin and they were dissolved. The solution was filtered to be sterilized with a 0.22 μm membrane filter. A container was filled with the filtrate to prepare a freeze-dried preparation. At the time when used, this freeze-dried preparation was dissolved in the above-described dissolving solution.

Example 4 Aqueous ophthalmic suspension

Preparation for an aqueous ophthalmic suspension containing rhSCF as an effective component Formulation

| | |
|---|---|
| rhSCF | 0.5 mg |
| sodium dihydrogenphosphate | 5 g |
| sodium chloride | 0.9 g |
| polysorbate 80 | 2 g |
| chlorobutanol | 0.3 g |
| sodium hydroxide | q.s. |

Sterilized purified water was added to make a total amount 100 ml. (pH 7.0)

Preparation Method

Sterilized pure water (80 ml) was heated, chlorobutanol was added thereto and dissolved, then sodium dihydrogenphosphate, sodium chloride and polysorbate 80 were added in succession and dissolved. The solution was cooled to room temperature. This solution was adjusted with sodium hydroxide to pH 5.0, then sterilized pure water was added to the solution to make the total amount of 100 ml. The mixture was filtered to be sterilized with a 0.22 μm membrane filter. Into the filtrate was dispersed uniformly a previously sterilized rhSCF freeze-dried preparation, and a container was filled with the resulted suspension to prepare an aqueous ophthalmic suspension.

Example 5 Eye ointment

Preparation of an eye ointment containing rhSCF as an effective component Formulation

| rhSCF | 10 g |
|---|---|
| liquid paraffin | 100 g |

White Vaseline was added to make a total amount 1000 g.

Preparation Method

Liquid paraffin and white Vaseline were previously heated for sterilization. Then rhSCF was fully mixed with liquid paraffin and the mixture was kneaded with white Vaseline sufficiently to prepare an eye ointment.

Example 6 Aqueous injection

Preparation of an aqueous injection containing rhSCF as an effective component: Formulation

| rhSCF | 100000 units |
|---|---|
| IL-2 | 10000 units |

Sterilized physiological saline was added to make a total amount 100 ml.

Preparation Method

To 100 ml of sterilized physiological saline were added rhSCF and freeze-dried IL-2 preparation and were dissolved, then the solution was filtered to be sterilized with a 0.22 μm membrane filter. Then, a container was filled with the resulting solution to prepare aqueous injection solution.

Test 1

Investigation of promoting effect on corneal epithelial healing of a normal rat with commercially available rmSCF, Test Example 1. Animal Nine SD male rats were used.

2. Test drug

Ten μg/ml of commercially available rmSCF dissolved in 0.1% BSA-containing PBS was used. The vehicle was used for control.

3. Method

Nine animals were subjected to general anesthesia, and each whole range of corneal epithelial layer (inner range of corneal limbus) of both eyes was scraped with an ophthalmic knife. Onto the right eye was dropped rmSCF and onto the left eye was dropped the vehicle respectively 4 times per day each in an amount of 5 μl for 3 days. For observation of the unhealed area, 0.1% fluorescein was dropped every 12 hours after scraping, the eye was photographed using a slit lamp, and the unhealing area of corneal epithelium was measured by an image analyzer. After completion of each observation, lomefloxacin hydrochloride-containing eye drop (trade name: Lomeflon, ophthalmic otologic solution, manufactured by Senju Pharmaceutical Co., Ltd.) was dropped for prevention of infection.

4. Statistical treatment

Paired t-test was used for significant difference assay compared with opposite eye (vehicle group).

5. Result

The ratio of corneal epithelial healing was shown in FIG. 1. At 12 hours after scraping, the corneal epithelial healing ratio of the rmSCF was approximately the same as that of the vehicle group, and at 24 hours or more after scraping, the corneal epithelial healing ratio of rmSCF was higher at any time and significant effect of corneal epithelial wound healing was observed.

Effect of the Invention

By systemic administration or local administration of the composition for treating cornea of the present invention to a patient suffering from corneal disorder, particularly corneal epithelium injury, the wound can be quickly restored, regenerated or returned to normal condition.

BRIEF DESCRIPTION OF THE DRAWING

FIG. 1 is a graph showing effect of SCF in curing of corneal epithelial deficiency. Horizontal line indicates time (hour) after corneal epithelial scraping and vertical line indicates the ratio (%) of healing area at respective times relative to the initial area immediately after corneal epithelial scraping.

Explanation of Mark ○:SCF ■:vehicle *:p<0.05 ** :p<0.01

What is claimed is:

1. A method of promoting corneal epithelial healing which comprises administering an effective amount of a composition comprising SCF and a pharmaceutically acceptable carrier to a subject suffering from corneal disorder.

2. The method according to claim 1, wherein the corneal disorder is corneal epithelial defect.

* * * * *